United States Patent [19]
Fujita

[11] Patent Number: 5,652,987
[45] Date of Patent: Aug. 5, 1997

[54] DECUBITUS ULCER PREVENTION DEVICE

[76] Inventor: Sanai Fujita, 107 Green Park Kotesashi, 12-1, 4-chome Kotesashi-cho, Tokorozawa-shi, Saitama-ken, Japan

[21] Appl. No.: 639,489

[22] Filed: Apr. 29, 1996

[30] Foreign Application Priority Data

May 17, 1995 [JP] Japan ................. 7-141390

[51] Int. Cl.$^6$ .................. A47C 21/04; A61F 7/00
[52] U.S. Cl. .................. 5/726; 5/652.2; 128/202.14; 128/202.16; 607/107
[58] Field of Search .................. 5/652.1, 652.2, 5/714, 723, 724, 726; 607/104, 107, 108, 114; 128/203.12, 845, 847, 202.16, 204.13, 204.14

[56] References Cited

U.S. PATENT DOCUMENTS

| | | | |
|---|---|---|---|
| 1,936,960 | 11/1933 | Bowman | 5/423 |
| 4,425,676 | 1/1984 | Crane | 5/689 |
| 5,514,346 | 5/1996 | Fujita | 422/124 |

FOREIGN PATENT DOCUMENTS

| | | | |
|---|---|---|---|
| 0491145 | 6/1992 | European Pat. Off. | 5/724 |
| 3612362 | 10/1987 | Germany | 5/423 |

*Primary Examiner*—Rodney M. Lindsey
*Assistant Examiner*—Robert G. Santos
*Attorney, Agent, or Firm*—Andrus, Sceales, Starke & Sawall

[57] ABSTRACT

The present invention relates to a decubitus ulcer prevention device, which comprises an air generator having a fan, an air mattress for receiving air, from the air generator, that is discharged at a surface through minute air discharge holes, and a hose for connecting the air mattress to the air generator. Along a flow path of the air that passes through the fan, are located, in order as named, a heater and an alkaline chlorine dioxide gas generator, in which is internally provided a ceramic body that is impregnated with an alkaline chlorine dioxide solution. Air that is heated, by passing through the heater, is brought into contact with the ceramic body, so that air that includes alkaline chlorine dioxide gas is thus supplied to the air mattress.

20 Claims, 16 Drawing Sheets

| TEST GERM | CATEGORY | ACTIVATED GERM COUNT ( PER GAUZE PAD ) | | | | | |
|---|---|---|---|---|---|---|---|
| | | AT START ✱1 | 20 MINUTES LATER | 1 HOUR LATER | 2 HOURS LATER | 3 HOURS LATER | 4 HOURS LATER |
| PSEUDOMONAS SERUGINOSA IFO 13275 | DECUBITUS ULCER PREVENTION DEVICE | $1.3 \times 10^8$ | $2.2 \times 10^7$ | $1.1 \times 10^6$ | $<10$ ✱2 | $<10$ | $<10$ |
| | COMPARISON DEVICE ✱3 | $1.1 \times 10^8$ | $4.8 \times 10^7$ | $3.9 \times 10^7$ | $2.4 \times 10^7$ | $3.6 \times 10^4$ | $8.3 \times 10^4$ |
| STAPHYLOCOCCUS AURERS IFO 12732 | DECUBITUS ULCER PREVENTION DEVICE | $9.6 \times 10^7$ | $5.8 \times 10^7$ | $1.8 \times 10^7$ | $<10$ | $<10$ | $<10$ |
| | COMPARISON DEVICE ✱3 | $8.3 \times 10^7$ | $1.5 \times 10^8$ | $1.5 \times 10^8$ | $2.5 \times 10^7$ | $6.3 \times 10^4$ | $<10$ |

✱1   The number of activated germs that were added to the gauze pads was measured, with the result of the measurement being calculated in terms of the number of activated germs at the beginning.

✱2   <10 : indicates that no germs were detected by the germ count method used for this experiment.

✱3   A ball that was impregnated with distilled water was inserted into vinyl chloride resin tube, and a test was conducted in the same manner.

FIG. 14

| CATEGORY | BEFORE ACTIVATION | 20 MINS. LATER | 1 HOUR LAER | 2 HRS. LATER. | 3 HRS. LATER |
|---|---|---|---|---|---|
| ANALYTE 1) | — | — | — | — | — |
| ANALYTE 2) | — | — | — | — | — |

— : NO COLOR REACTION DETECTED

F I G. 1 5

DECUBITUS ULCER PREVENTION DEVICE

BACKGROUND OF THE INVENTION

Field of the Invention

1. The present invention relates to a device for supplying deodorized, sterilized air that contains alkaline chlorine dioxide gas for drying, deodorizing and sterilizing the human epidermis and clothing, bedding, etc., to clean them and to prevent the occurrence of decubitus ulcers.

2. Related Arts

When it is physically difficult for people, such as bedridden elderly persons or patients with advanced diseases, to raise themselves without help and as a result they are confined to their beds for extended periods of time, blood circulation is impeded at those portions of their bodies that press against their beds. Then, when those areas become hot and are kept moist by perspiration, or when wounds or insect bites in those areas become infected, so-called decubitus ulcers occur.

Furthermore, when a patient is confined to bed for a long time, the patient's clothing, such as underwear, and bed sheets and other bedding become soiled, bad odors are generated, and the load placed on care providers and nursing personnel is increased. In addition, the possibility that care providers and nursing personnel may contract a viral infection, particularly MRSA, becomes a serious problem.

Therefore, as is shown, for example, in FIG. 16, devices have been produced and are on the market that provide for air, which is supplied by an air generator 1, to be discharged from an air mattress 2 having a waveform surface.

According to the claims made for this device, as the surface of the air mattress 2 has a waveform shape, the area of a human body that comes into contact with the mattress is diminished, and this prevents the circulation of blood from being interrupted. Further, as air is discharged from the waveform surface, overheating of the body and the moisture that is produced by perspiration can be prevented.

Proposed in addition are members, such as a mattress, that contact the body of a patient. For one such decubitus ulcer prevention device (Japanese Unexamined Patent Publication No. Hei 5-84121), a plurality of holes are formed in a mattress, and slidably located in these holes are pressure receiving members, which have recesses, to provide support for a human body. As another patient care item (Japanese Unexamined Patent Publication No. Hei 5-154178), a mattress has a surface that is made of silk.

In the above conventional decubitus ulcer prevention devices, however, the heating of a human body and the moisture that is caused by perspiration, and the interruption of blood circulation at a body portion that presses against a bed can not be satisfactorily prevented. Furthermore, the deodorization of the underwear and the bedclothes of patients and the sterilization that is required to destroy germs that propagate in them, and the protection of care providers and nursing personnel from viral infections, etc., can not be carried out.

SUMMARY OF THE INVENTION

To resolve the above conventional shortcomings, it is one object of the present invention to provide a device having a simple structure that ensures the drying, the deodorizing and the sterilizing of a human body, and clothing and bedding to keep them clean and to prevent the occurrence of decubitus ulcers.

To achieve the above object, according to the present invention, provided is a decubitus ulcer prevention device, which comprises:

an air generator having a fan, an air mattress for receiving air, from the air generator, that is discharged at a surface through minute air discharge holes, and a hose for connecting the air mattress to the air generator, wherein, along a flow path of the air that passes through the fan, are located, in order as named, a heater and an alkaline chlorine dioxide gas generator, in which is internally provided a ceramic body that is impregnated with an alkaline chlorine dioxide solution, whereby air that is heated, by passing through the heater, is brought into contact with the ceramic body, so that air that includes alkaline chlorine dioxide gas is thus supplied to the air mattress.

In addition, to achieve the object, according to the present invention, provided is a decubitus ulcer prevention device, which comprises:

an air generator having a fan, an air mattress for receiving air, from the air generator, that is discharged at a surface through minute discharge holes, and a hose for connecting the air mattress with the air generator, wherein, along a flow path of the air that passes through the fan, is located an alkaline chlorine dioxide gas generator, in which a ceramic body that is impregnated with a citric acid solution is provided on the fan side and a ceramic body that is impregnated with an alkaline chlorine dioxide solution is provided following the ceramic body that is impregnated with a citric acid solution, whereby air that passes through the fan contacts the ceramic bodies, so that air that includes alkaline chlorine dioxide gas is thus supplied to the air mattress.

The alkaline chlorine dioxide gas generator is stored detachably in the air generator.

The alkaline chlorine dioxide gas generator is installed outside the air generator and is so connected to the hose as to be detachable.

A unit for supplying an alkaline chlorine dioxide solution to the ceramic body is detachably attached to the alkaline chlorine dioxide gas generator, and formed in the ceramic body is a solution supply groove for supplying the alkaline chlorine dioxide solution to a surrounding side portion of the ceramic body.

A unit for supplying a citric acid solution to the ceramic body is detachably attached to the alkaline chlorine dioxide gas generator, and formed in the ceramic body is a solution supply groove for supplying the citric acid solution to a surrounding side portion of the ceramic body.

The alkaline chlorine dioxide solution that is used to permeate the ceramic body, which is impregnated with the alkaline chlorine dioxide solution, has a calculated chlorine dioxide content of 50 ppm to 1000 ppm.

The citric acid solution that is used to permeate the ceramic body is adjusted to pH 2 to pH 5.

The ceramic bodies are columnar in shape, and in cross section have a plurality of longitudinal through holes.

The ceramic bodies are formed from alkaline ceramics that contain at least one material selected from a group consisting of animal bone powder, shell powder, limestone powder, and coral powder.

The alkaline ceramic contains animal bone powder as the main activated element.

The alkaline ceramic contains at least one ceramic selected from a group consisting of silica gel, alumina, and zeolite.

As is described above, according to the present invention, the heater and the alkaline chlorine dioxide gas generator are located along the air flow path from the fan. The air that is driven by the fan and that is heated by the heater contacts the ceramic body, which is internally provided in the alkaline chlorine dioxide gas generator, that is impregnated with an alkaline chlorine dioxide solution, so that air can be supplied that contains alkaline chlorine dioxide gas for deodorization, sterilization, and drying.

Further, according to the present invention, located along the air flow path from the fan is the alkaline chlorine dioxide gas generator, in which are provided the ceramic body that is impregnated with a citric acid solution and the ceramic body that is impregnated with an alkaline chlorine dioxide solution, wherein the air from the fan contacts the ceramic bodies so that air can be supplied to the air mattress that contains alkaline chlorine dioxide gas for deodorization, sterilization, and drying.

The alkaline ceramic bodies react to heat extremely easily. When air that is heated to 30° C. to 50° C., for example, contacts a ceramic body that is impregnated with an alkaline chlorine dioxide solution, alkaline chlorine dioxide gas is generated.

In addition, the alkaline ceramic bodies react easily to gas that contains citric acid. Even when air that contains citric acid is at an ordinary temperature when it contacts a ceramic body that is impregnated with the alkaline chlorine dioxide solution, alkaline chlorine dioxide gas is generated.

The air that contains the alkaline chlorine dioxide gas, which is generated by the alkaline chlorine dioxide gas generator, is passed through the hose and is discharged through the minute discharge holes in the air mattress.

It is well known that chlorine dioxide gas demonstrates excellent deodorization and sterilization effects, that heated air provides a drying effect and kills ticks, and that alkaline air accelerates the drying effect and also provides a sterilization effect. The present invention utilizes the synergistic effect acquired by employing together chlorine dioxide gas, warm air, and alkaline air.

Since air that contains alkaline chlorine dioxide gas is discharged through minute holes in the surface of the air mattress, and since almost all parts of a patient's body are touched by the gas and are dried, the patient's body is prevented from becoming hot and from becoming damp from perspiration.

Further, the injured portion of a person's body can be dried and sterilized, and healed, and the propagation of contagion can be prevented, so that effective sterilization is performed, and care providers and nursing personnel can be protected from becoming infected by germs and viruses.

Also, the deodorization, sterilization and drying of the underwear of bedridden elderly persons or patients with advanced diseases, and their bedclothes are performed, so that the load placed on care providers or nursing personnel can be reduced.

In the present invention an air mattress is employed that has a wave shaped surface to reduce the area that contacts a patient's body, and an interruption in the circulation of blood and a condition of high humidity are thus prevented so that decubitus ulcers will not occur.

According to the present invention, the easy supply of air for deodorization and sterilization is ensured. By using this air for drying, deodorizing and sterilizing, a patient's body and the patient's clothing and bedding can be kept clean, and the occurrence of decubitus ulcers can be prevented.

Furthermore, according to the present invention, the propagation of contagious diseases is prevented, effective sterilization is performed, and care providers and nursing personnel can be protected from viral infections.

BRIEF DESCRIPTION OF THE DRAWINGS

FIG. 14 is a diagram showing the results of the measurements to determine the number of living germs when the experiment was conducted by using the model in FIG. 13;

FIG. 15 is a diagram showing the results of the measurements to determine the remaining amount of chlorine dioxide when the experiment was conducted by using the model in FIG. 13.

DETAILED DESCRIPTION OF THE PREFERRED EMBODIMENTS

The preferred embodiments of the present invention will now be described while referring to the accompanying drawings. The present invention is, however, not limited to these embodiments.

Figure 1:
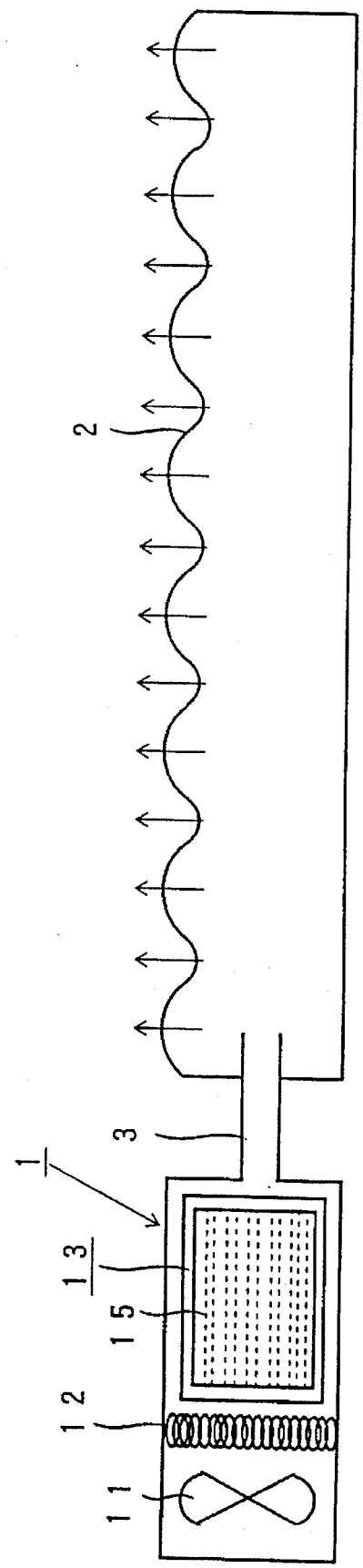
FIG. 1 is a diagram illustrating an arrangement for a decubitus prevention device according to a first embodiment of the present invention.
Figure 2:
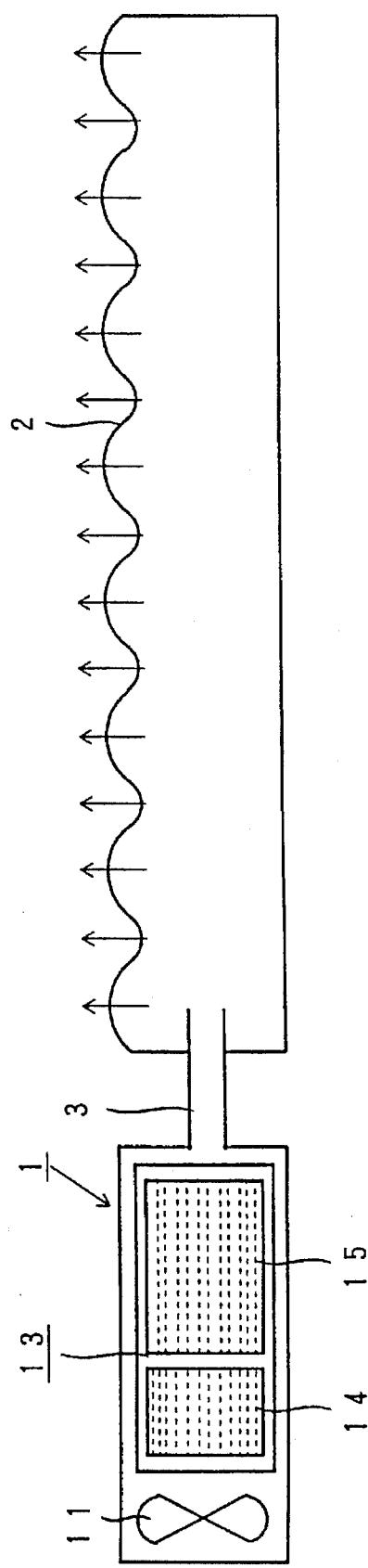
FIG. 2 is a diagram illustrating an arrangement for a decubitus prevention device according to a second embodiment of the present invention.

FIG. 1 is a diagram illustrating a decubitus ulcer prevention device according to a first embodiment of the present invention, and FIG. 2 is a diagram illustrating a decubitus ulcer prevention device according to a second embodiment of the present invention.

Figure 3:
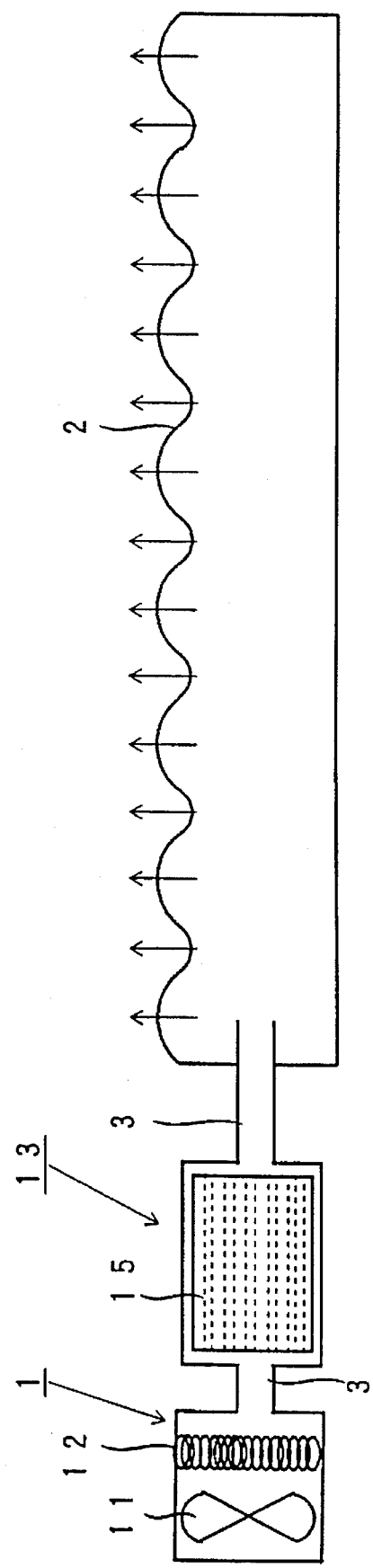
FIG. 3 is a diagram illustrating another location example for an alkaline chlorine dioxide gas generator according to the first embodiment of the present invention.
Figure 4:
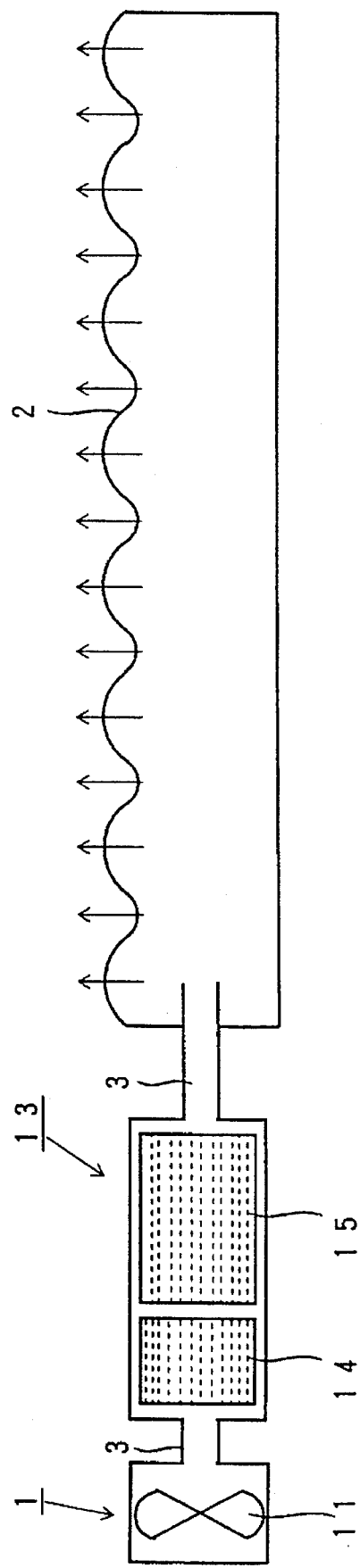
FIG. 4 is a diagram illustrating another location example for an alkaline chlorine dioxide gas generator according to the second embodiment of the present invention.

FIG. 3 is a diagram illustrating a different example arrangement for an alkaline chlorine dioxide gas generator according to the first embodiment of the present invention, and FIG. 4 is a diagram illustrating a different example arrangement of an alkaline chlorine dioxide gas generator according to the second embodiment of the present invention.

In these drawings, reference number 1 denotes an air generator; 2, an air mattress; 3, a hose; 11, a fan; 12, a heater; 13, an alkaline chlorine dioxide gas generator; 14, a ceramic body that is impregnated with a citric acid solution; and 15, a ceramic body that is impregnated with an alkaline chlorine dioxide solution.

As is shown in FIG. 1, the air generator 1 according to the first embodiment comprises the fan 11, the heater 12, and the alkaline chlorine dioxide gas generator 13, in which is provided the ceramic body 15, which is impregnated with an alkaline chlorine dioxide solution and which is so installed in the air generator 1 as to be detachable therefrom.

Although the structure of the air generator 1 is complicated because the alkaline chlorine dioxide gas generator 13 is detachably retained in the air generator 1, as is described above, the decubitus ulcer prevention device of the present invention can be compactly made so that it is easy to carry and to store and the replacement of the ceramic body 15 is facilitated.

As is shown in FIGS. 3 and 4, the alkaline chlorine dioxide gas generator 13 can be installed outside the air generator 1, and as a cartridge can be detachably connected at a proper position to a hose.

With this arrangement, although the decubitus ulcer prevention device of the present invention is not easy to carry and to store, as the alkaline chlorine dioxide gas generator 13 is an independent component of the air generator 1, the replacement of the ceramic body 15 that is provided in the alkaline chlorine dioxide gas generator 13 is facilitated, and the effect provided by the device of the present invention can be obtained.

The heater 12 is located beside the fan 11 because, as an alkaline ceramic reacts easily with heat, the air from the fan 11 can be heated by the heater 12 and can be brought into contact with the ceramic body 15, which is impregnated with an alkaline chlorine dioxide solution, so as to increase the amount of alkaline chlorine dioxide gas that is generated at the ceramic body 15.

The original temperature of the heated air is preferably 30° C. to 50° C., but the air that contains the alkaline dioxide gas, and has passed from the alkaline chlorine dioxide gas generator 13 and through the hose 3, is discharged from the surface of the air mattress 2 at about 22° C. to 27° C., which for a human body is a comfortable temperature range. The decubitus ulcer prevention device of the present invention is the preferable device, especially when it is used during a period, such as winter, when the temperature is low.

As is shown in FIG. 2, the air generator 1 according to the second embodiment comprises the fan 11 and the alkaline chlorine dioxide gas generator 13. Internally, the alkaline chlorine dioxide gas generator 13 has not only the ceramic body 15, which is impregnated with the alkaline chlorine dioxide solution, but also a ceramic body 14, which is impregnated with a citric acid solution, on the side near the fan 11. The heater 12 is not provided therein.

The alkaline chlorine dioxide gas generator 13, wherein internally provided are the ceramic body 15, which is impregnated with an alkaline chlorine dioxide solution, and the ceramic body 14, which is impregnated with a citric acid solution, is so installed in the air generator 1 as to be detachable therefrom.

With this arrangement, since air at an ordinary temperature, rather than air that is heated by the heater 12, is brought into contact with the ceramic body 15, which is impregnated with an alkaline chlorine dioxide solution, the amount of alkaline chlorine dioxide gas that is generated at the ceramic body 15 is reduced.

Therefore, provided on the side near the fan 11 is the ceramic body 14, which is impregnated with a citric acid solution and generates citric gas to accelerate the generation of alkaline chlorine dioxide gas, so that an air stream that contains citric acid is directed at the ceramic body 15, which is impregnated with an alkaline chlorine dioxide solution, to increase the amount of alkaline chlorine dioxide gas that is generated.

The preferable acid for the acid solution is a volatile organic acid; and taking virulence, odors, etc., into account, citric acid is used, even though another acid may be employed. A desirable citric acid solution is adjusted so that it has a pH value of pH 2 to pH 5, or, more preferably, either pH 3 or pH 4

Since people feel uncomfortable when their bodies are exposed to heated air during a high temperature period, such as in summer, the device of the present invention utilizes air at normal temperatures. The device of the present invention is therefore appropriate for use even in periods during which the temperature is higher than normal.

As is shown in FIG. 4, the alkaline chlorine dioxide gas generator 13 can be installed outside the air generator 1, and, as a cartridge, can be detachably connected to the hose 3 at a proper position.

In this manner, although the device of the present invention is not easy to carry and to store, as the alkaline chlorine dioxide gas generator 13 is independent of the air generator 1, the replacement of the ceramic bodies 14 and 15 that are provided in the alkaline chlorine dioxide gas generator 13 is facilitated, and the effects that are provided by the device of the present invention can be constantly maintained.

An air flow adjustor may be installed for the air generator 1 for the adjustment, as desired, of the air flow rate and the volume of the gas that is discharged from the air mattress. With this arrangement, the volume of gas that is discharged from the surface of the air mattress, and the degree of inflation and the shape of the air mattress can be freely changed.

Furthermore, a timer may be provided for the air generator 1 and an operating time for the device of the present invention may be set in advance, so that the period during which the device is operated can be freely changed.

Figure 5A:
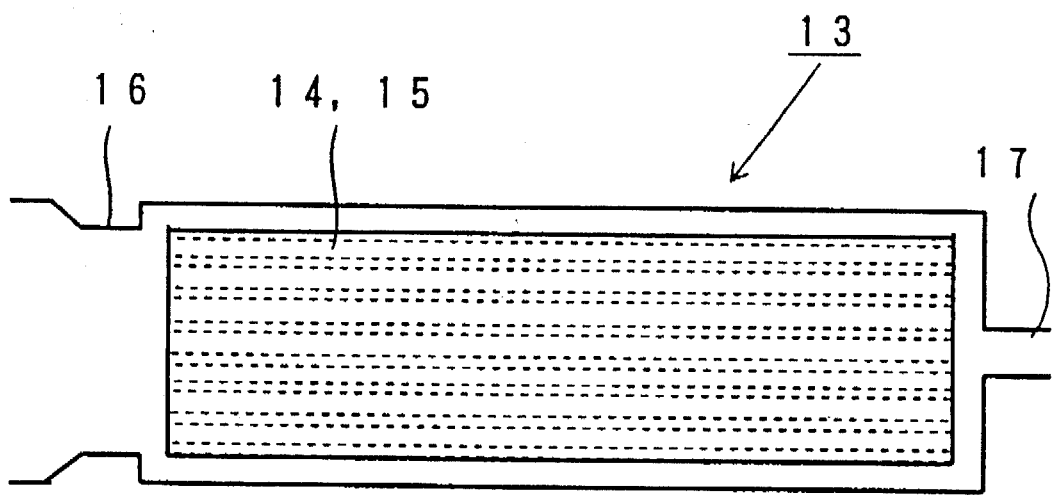
FIGS. 5A and 5B are cross sections of example arrangements for the alkaline chlorine dioxide gas generator according to the present invention, with FIG. 5A more specifically showing an alkaline chlorine dioxide gas generator that is provided in an air generator, and with FIG. 5B more specifically showing an alkaline chlorine dioxide gas generator that is provided outside an air generator to which is connected by a hose.
Figure 5B:
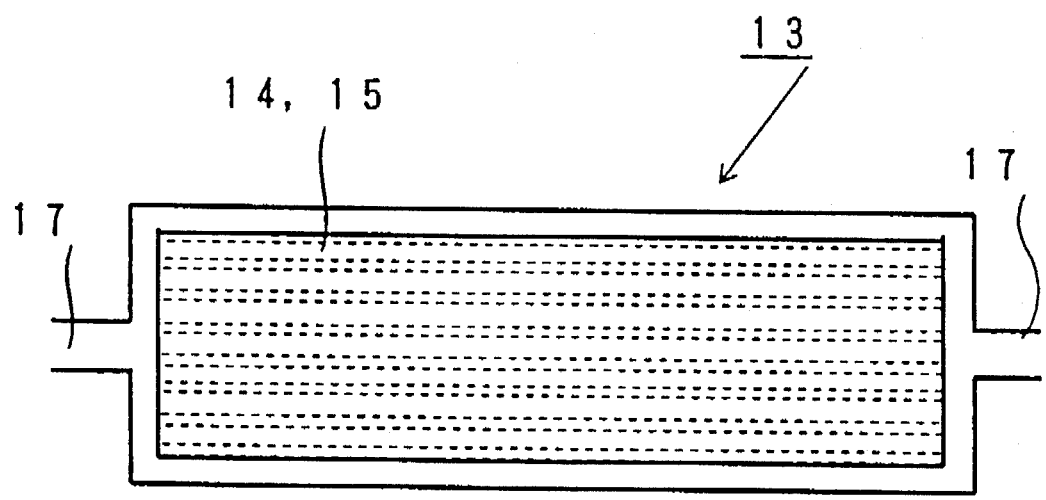

FIGS. 5A and 5B are cross sections of example arrangements of the alkaline chlorine dioxide gas generator 13. In FIG. 5A is shown the arrangement for an alkaline chlorine dioxide gas generator 13 that is retained in the air generator 1, and in FIG. 5B is shown the arrangement for an alkaline dioxide gas generator 13 that is located outside the air generator 1 and is connected to the hose 3.

As is shown, the ceramic bodies 14 and 15, which are respectively impregnated with a citric acid solution and an alkaline chlorine dioxide solution, are provided in the alkaline chlorine dioxide gas generator 13.

The alkaline chlorine dioxide gas generator 13 that is retained in the air generator 1 is coupled at one end with an air outlet 16 for the fan 11 and at the other end is coupled via a connector 17 to the hose 3, as is shown in FIG. 5A.

When the citric acid solution content and the alkaline chlorine dioxide solution content of the respective ceramic bodies 14 and 15 are reduced, they must be replaced by new ceramic bodies 14 and 15 that are impregnated with the named solutions.

With this arrangement, although the structure of the alkaline chlorine dioxide gas generator 13 is simplified, the citric acid solution content and the alkaline chlorine dioxide solution content are limited, and thus the ceramic bodies 14 and 15 must be replaced frequently.

The alkaline chlorine dioxide gas generator 13, which is installed outside the air generator 1 and is coupled with the hose 3, is connected to the hose 3 at both ends via the connectors 17, as is shown in FIG. 5B.

Since the alkaline chlorine dioxide gas generator 13 is formed as a cartridge so that it can be detachably coupled with the hose 3 via the connectors 17, the replacement of the ceramic bodies is facilitated and a device with excellent usability can therefore be provided.

Figure 6A:
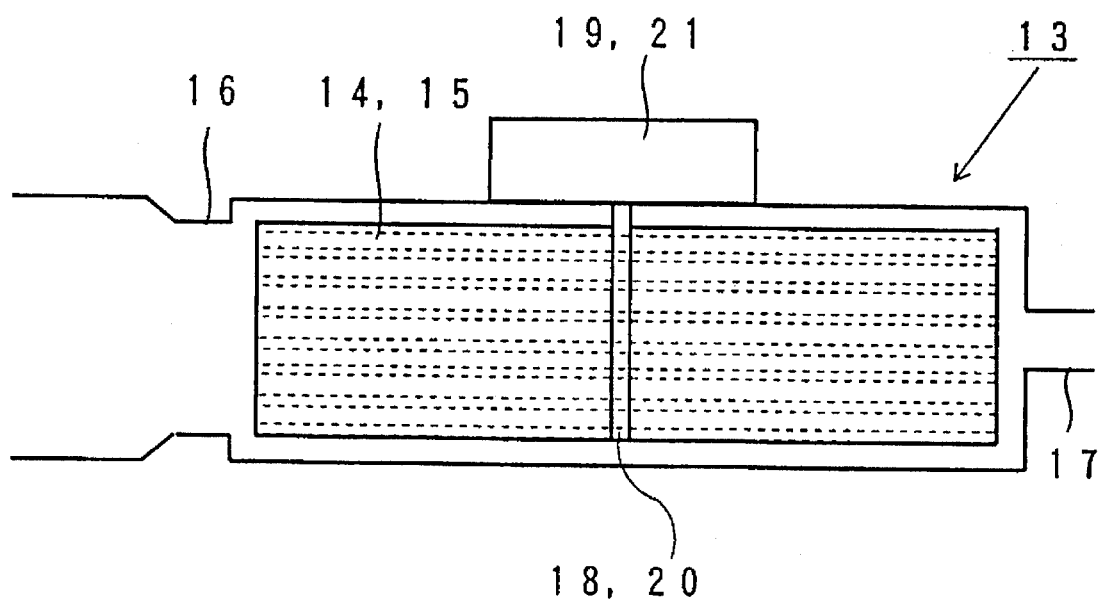
FIGS. 6A and 6B are cross sections of example arrangements wherein a solution supplying device is attached to the alkaline chlorine dioxide gas generator according to the present invention, with FIG. 6A more specifically showing an alkaline chlorine dioxide gas generator that is provided in an air generator, and with FIG. 6B more specifically showing an alkaline chlorine dioxide gas generator that is provided outside an air generator to which it is connected by a hose.
Figure 6B:
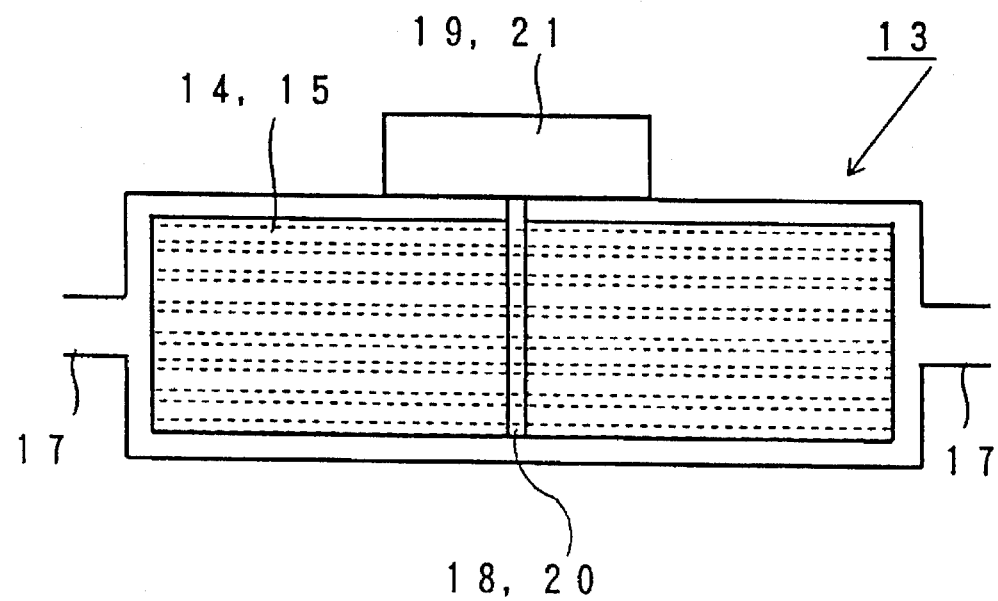

FIGS. 6A and 6B are cross sections of other example arrangements for the alkaline chlorine dioxide gas generator 13. In FIG. 6A is shown the arrangement of an alkaline chlorine dioxide gas generator 13 that is provided in the air generator 1, and in FIG. 6B is shown the arrangement of an alkaline dioxide gas generator 13 that is located outside the air generator 1 and is connected to the hose 3.

As is shown in FIGS. 6A and 6B, solution supply grooves 18 and 20, along which are respectively supplied a citric acid solution and an alkaline chlorine dioxide solution, are formed in the ceramic bodies 14 and 15, which are located in the alkaline chlorine dioxide gas generator 13. Solution supply units 19 and 21 are detachably mounted at proper locations on the alkaline chlorine dioxide gas generator 13, so that a citric acid solution and an alkaline chlorine dioxide solution can be respectively supplied along the solution supply grooves 18 and 20 to the ceramic bodies 14 and 15.

According to this arrangement, although the structure of the alkaline chlorine dioxide gas generator 13 is complicated, as a citric acid solution and an alkaline chlorine dioxide solution are fed to the ceramic bodies 14 and 15 from the solution supply units 19 and 21, the period before the ceramic bodies 14 and 15 must be replaced can be extended.

Further, since the solution supply units 19 and 21 are detachably mounted on the alkaline chlorine dioxide gas generator 13, the supplementation of the citric acid solution and the alkaline chlorine dioxide solution for the solution supply units 19 and 21 can be facilitated.

A citric acid solution and an alkaline chlorine dioxide solution are fed from the solution supply units 19 and 21 along the solution supply grooves 18 and 20, which are formed in the ceramic bodies 14 and 15, and completely permeate the ceramic bodies 14 and 15 via through holes 22 and 23, which are formed in the respective ceramic bodies 14 and 15.

Figure 7A:
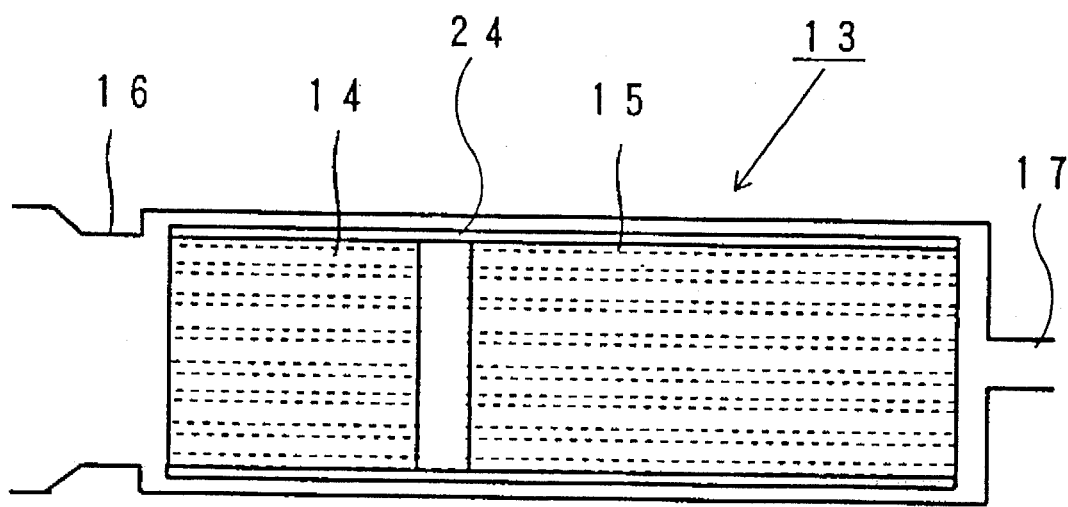
FIGS. 7A and 7B are cross sections of example arrangements for the alkaline chlorine dioxide gas generator according to the present invention, wherein a ceramic body that is impregnated with a citric acid solution is linked to a ceramic body that is impregnated with an alkaline chlorine dioxide solution, with FIG. 7A more specifically showing an alkaline chlorine dioxide gas generator that is provided in an air generator, and with FIG. 7B more specifically showing an alkaline chlorine dioxide gas generator that is provided outside an air generator to which it is connected by a hose.
Figure 7B:
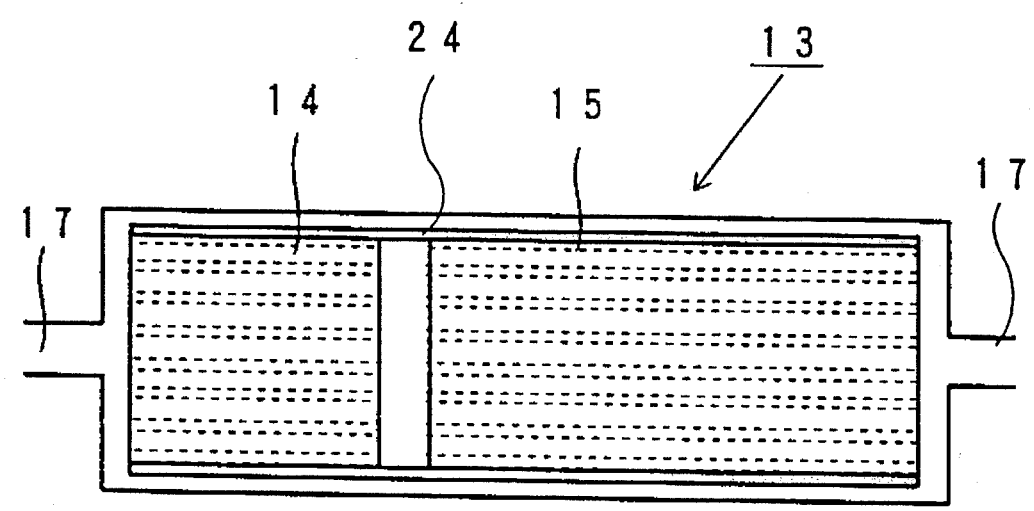

FIGS. 7A and 7B are cross-sectional views of example arrangements wherein the ceramic body 14 that is impregnated with a citric acid solution and the ceramic body 15 that is impregnated with an alkaline chlorine dioxide solution are coupled together and are located in the alkaline chlorine dioxide gas generator 13. In FIG. 7A is shown the arrangement for an alkaline chlorine dioxide gas generator 13 that is retained in the air generator 1, and in FIG. 7B is shown the arrangement for an alkaline dioxide gas generator 13 that is located outside the air generator 1 and is connected to the hose 3.

As is illustrated, in the alkaline chlorine dioxide gas generator 13, the ceramic body 14 that is impregnated with a citric acid solution is located on the side nearest the fan 11, while the ceramic body 15 that is impregnated with an alkaline chlorine dioxide solution is located on the side nearest the hose, and both ceramic bodies are fixed by using non-woven cloth 24.

The ratio of the size of the ceramic body 14 that is impregnated with a citric acid solution to the size of the ceramic body 15 that is impregnated with an alkaline chlorine dioxide solution is preferably about 3 to 7.

Air that is driven by the fan 11 contacts the ceramic body 14 that is impregnated with a citric acid solution and thereafter contains citric acid gas. The air and citric acid gas mixture then contacts the ceramic body 15 that is impregnated with an alkaline chlorine dioxide solution and alkaline chlorine dioxide gas is generated. The air, which now contains alkaline chlorine dioxide gas, is thereafter supplied to the hose 3.

Figure 8A:
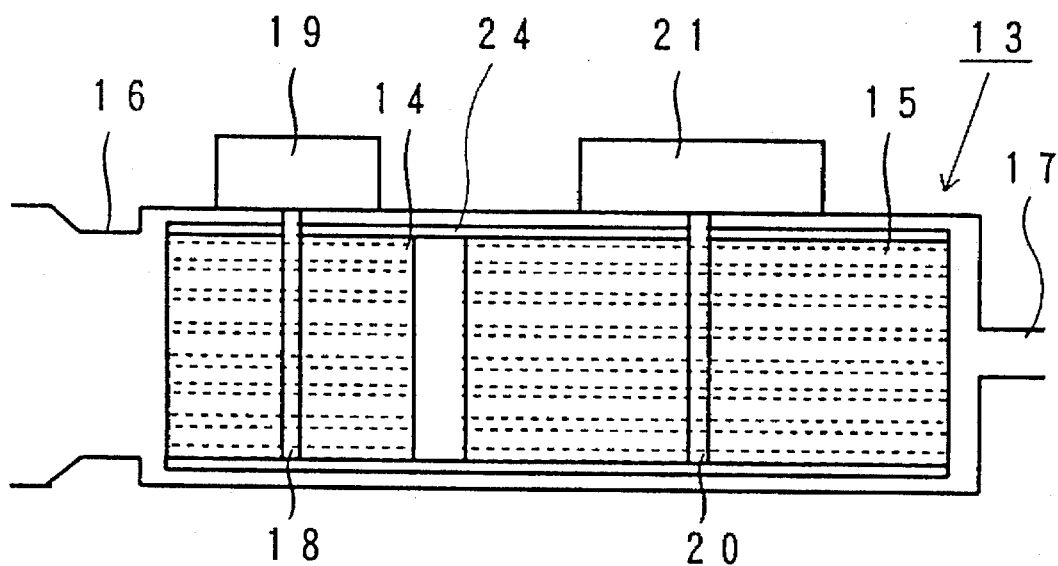
FIGS. 8A and 8B are cross sections of example arrangements for the alkaline chlorine dioxide gas generator according to the present invention, wherein ceramic bodies, to each of which a solution supplying device is attached, are positioned in line, with FIG. 8A more specifically showing an alkaline chlorine dioxide gas generator that is provided in an air generator, and with FIG. 8B more specifically showing an alkaline chlorine dioxide gas generator that is provided outside an air generator to which is connected by a hose.
Figure 8B:
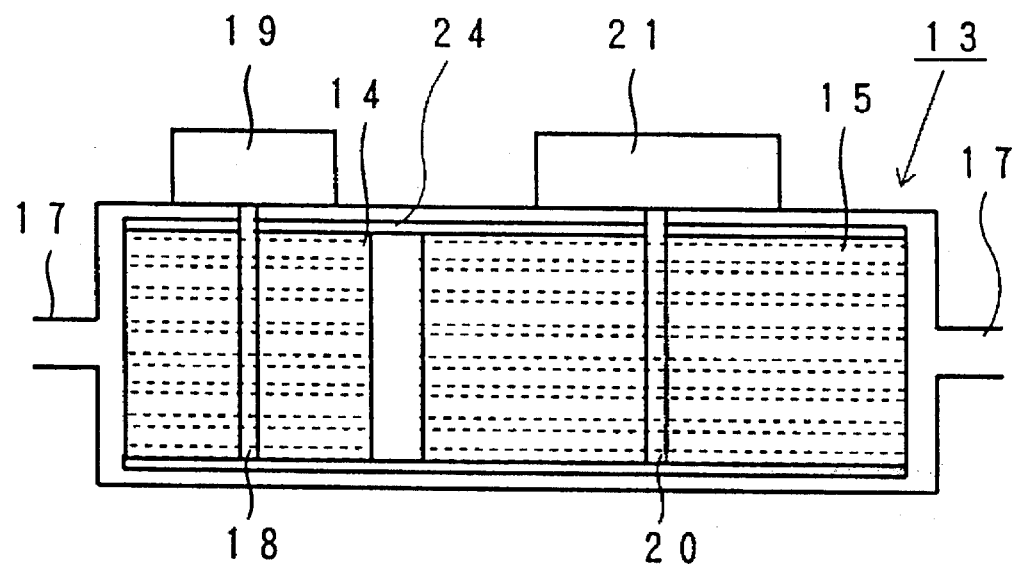

FIGS. 8A and 8B are cross-sectional views of example arrangements wherein the citric acid solution supply unit 19 and the alkaline chlorine dioxide solution supply unit 21 are mounted on the alkaline chlorine dioxide gas generator 13, with the ceramic bodies 14 and 15 being coupled together and located in the alkaline chlorine dioxide gas generator 13, so that a citric acid solution and an alkaline chlorine dioxide solution are supplied along the solution supply grooves 18 and 20 by the solution supply units 19 and 21 respectively. In FIG. 8A is shown the arrangement for an alkaline chlorine dioxide gas generator 13 that is retained in the air generator 1, and in FIG. 8B is shown the arrangement for an alkaline dioxide gas generator 13 that is located outside the air generator 1 and is connected to the hose 3. These arrangements have already been described in detail and no further explanation will be given here.

Figure 9A:
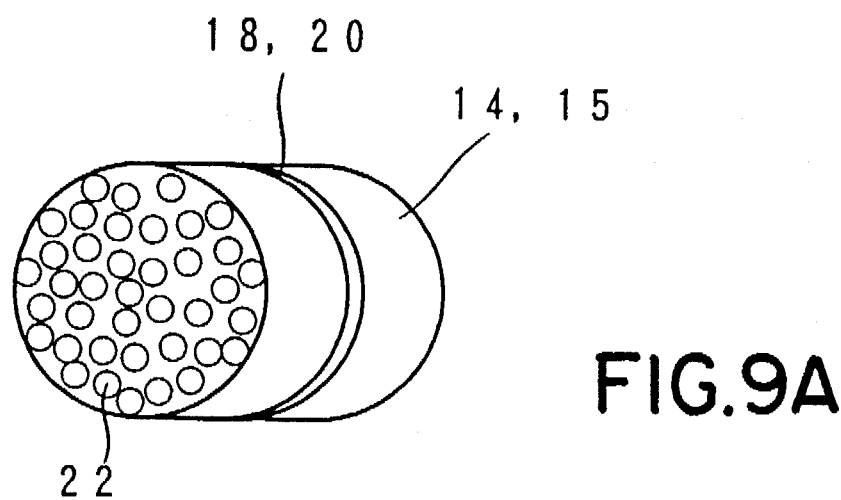
FIGS. 9A and 9B are diagrams showing the structural outlines of ceramic body examples according to the present invention, with FIG. 9A more specifically showing an example ceramic body in which a solution supply groove is formed, and with FIG. 9B more specifically showing an example ceramic body in which such a solution supply groove is not formed.
Figure 9B:
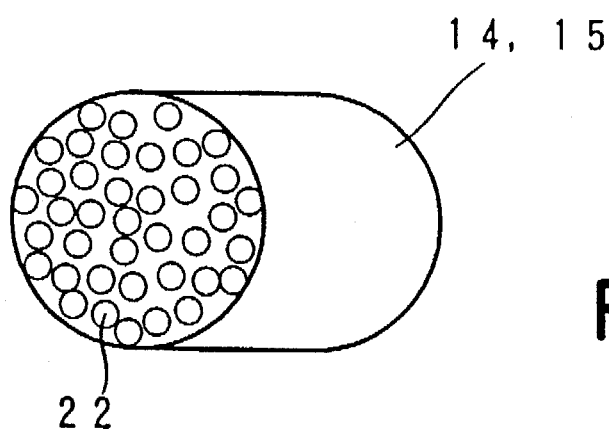
Figure 10A:
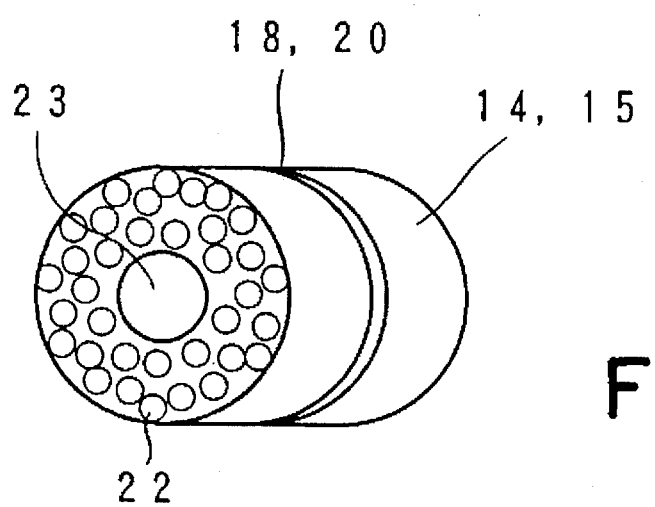
FIGS. 10A and 10B are diagrams showing the structural outlines of other ceramic body examples according to the present invention, with FIG. 10A more specifically showing an example ceramic body in which a solution supply groove is formed, and with FIG. 10B more specifically showing an example ceramic body in which such a solution supply groove is not formed.
Figure 10B:
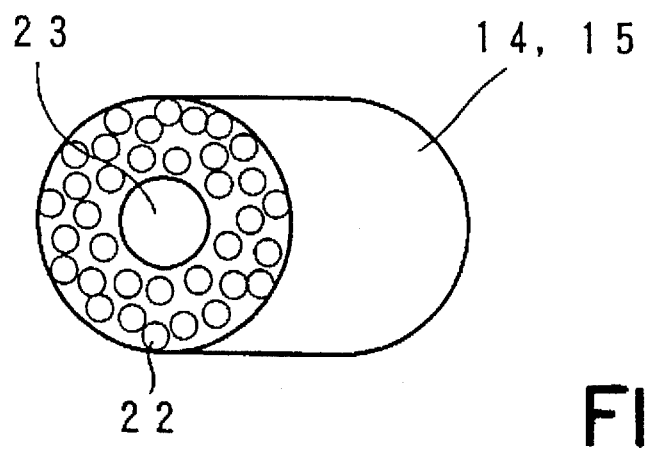

FIGS. 9A and 9B are diagrams illustrating examples for the ceramic bodies 14 and 15, and FIGS. 10A and 10B are diagrams illustrating other examples for the ceramic bodies 14 and 15. In FIGS. 9A and 10A are shown the ceramic bodies 14 and 15 wherein are formed the solution supply grooves 18 and 20 along which a citric acid solution and an alkaline chlorine dioxide solution are supplied by the solution supply units 19 and 21.

As is shown in FIGS. 9A and 9B, the ceramic bodies 14 and 15 are columnar, cylindrical, for example, and a plurality of the through holes 22 are provided in their cross sections in the longitudinal direction. It is desirable that multiple through holes 22 be formed for good ventilation.

When many of the comparatively small through holes 22 that have an identical diameter are formed longitudinally in the ceramic bodies 14 and 15, after air has passed through the through holes 22 it contains more alkaline chlorine dioxide gas, and the deodorizing and sterilizing effects are accordingly increased.

As is shown in FIGS. 10A and 10B, a through hole 23 having a large diameter is also provided in the center of the cross section of each of the ceramic bodies 14 and 15, and many through holes 22 having a smaller diameter are arranged around the large through hole 23.

With this arrangement, the backflow to the fan 11 of an air stream that contains alkaline chlorine dioxide gas can be prevented.

Figure 11A:
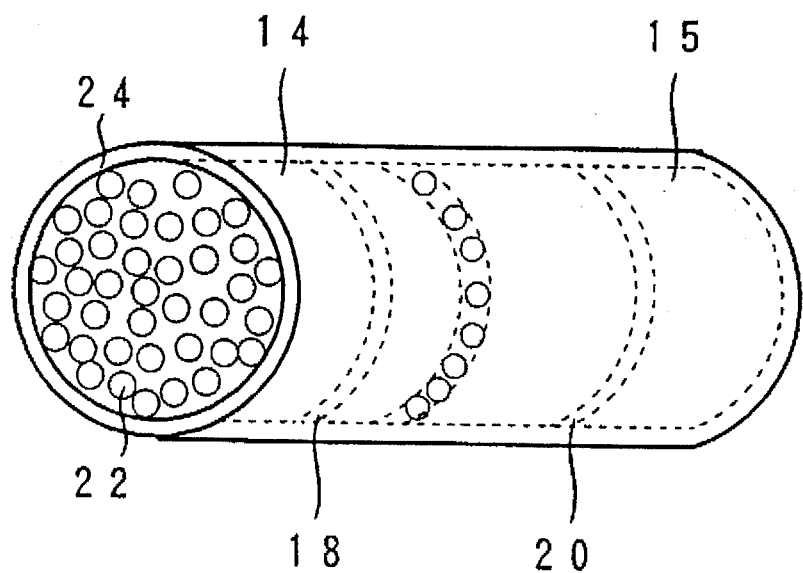
FIGS. 11A and 11B are cross sections of example arrangements wherein the ceramic body of the present invention that is impregnated with a citric acid solution and the ceramic body of the present invention that is impregnated with an alkaline chlorine dioxide solution are secured with a non-woven fabric and are linked together, with FIG. 11A more specifically showing an example ceramic body in which a solution supply groove is formed, and with FIG. 11B more specifically showing an example ceramic body in which a solution supply groove is not formed.
Figure 11B:
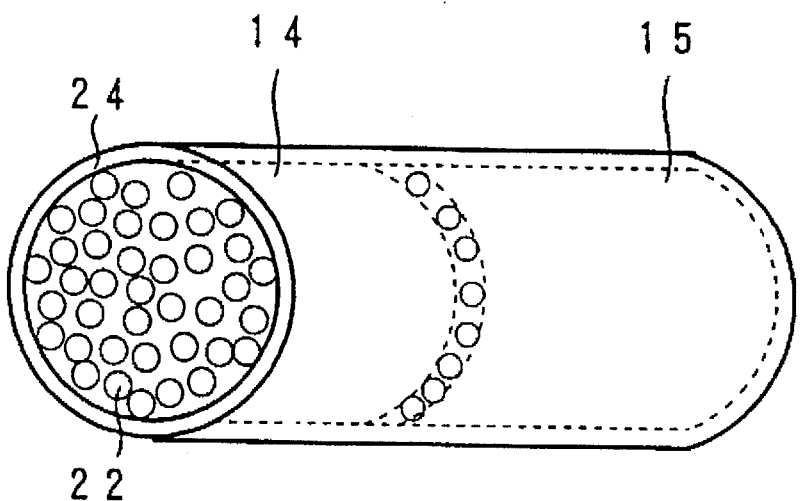

FIGS. 11A and 11B are cross-sectional views of example arrangements wherein the ceramic body 14 that is impregnated with a citric acid solution, and the ceramic body 15 that is impregnated with an alkaline chlorine dioxide solution are coupled together with, and fixed by the non-woven fabric 24. In FIG. 11A is shown an example wherein the solution supply grooves 18 and 20 are formed in the ceramic bodies 14 and 15.

Figure 12A:
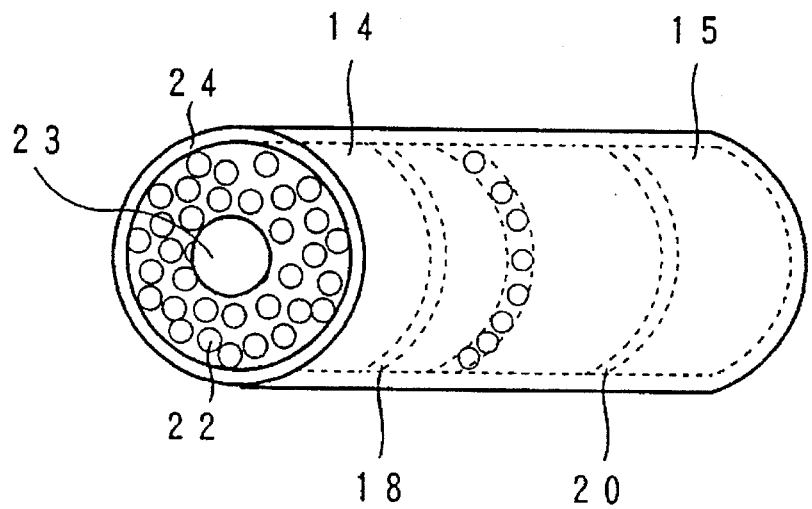
FIGS. 12A and 12B are cross sections of other example arrangements wherein the ceramic body of the present invention that is impregnated with a citric acid solution and the ceramic body of the present invention that is impregnated with an alkaline chlorine dioxide solution are secured with a non-woven fabric and are linked together, with FIG. 12A more specifically showing an example ceramic body in which a solution supply groove is formed, and with FIG. 12B more specifically showing an example ceramic body in which a solution supply groove is not formed.
Figure 12B:
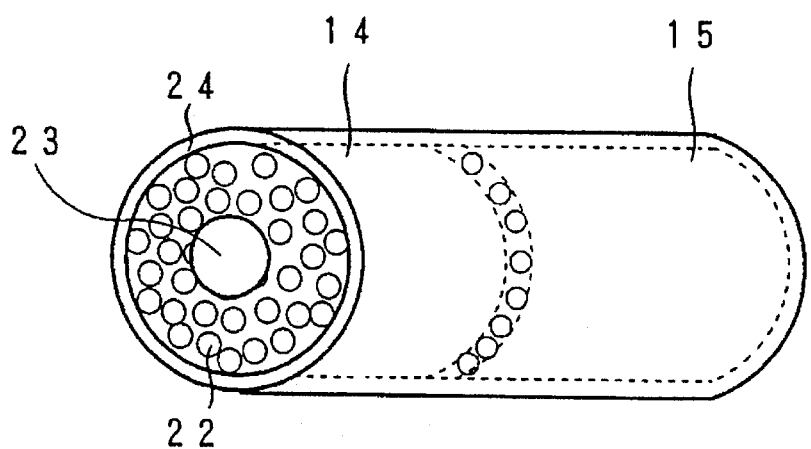

FIGS. 12A and 12B are cross-sectional views of other example arrangements wherein the ceramic body 14 that is impregnated with a citric acid solution, and the ceramic body 15 that is impregnated with an alkaline chlorine dioxide solution are coupled together with, and fixed by the non-woven fabric 24. In FIG. 12A is shown an example wherein the solution supply grooves 18 and 20 are formed in the ceramic bodies 14 and 15.

The details of these arrangements have been described above and no further explanation will be given here.

Chlorine dioxide is normally produced by an acid that acts on sodium chlorate or on calcium chlorate acid. Since the chlorine dioxide that is thus obtained is very explosive and dangerous, it must be handled very carefully.

Therefore, chlorine dioxide gas that has been stabilized in alkaline water, and that is thereafter kept in the stabilized state, has been developed (the gas is hereinafter referred to as "stabilized chlorine dioxide gas"). That chlorine dioxide gas is excellent for deodorization and sterilization is well known.

According to this invention, a ceramic body is immersed in the stabilized chlorine dioxide solution to obtain a ceramic body that is impregnated with the stabilized chlorine dioxide solution.

The pH value of the alkaline stabilized chlorine dioxide solution of the present invention is preferably pH 8 to pH 9.6. If the pH value is lower than 8 or higher than 9.6, the liberation of chlorine dioxide gas tends to be difficult, and the amount of chlorine dioxide gas that is contained in the heated air stream tends to be decreased.

The impregnation content of an alkaline chlorine dioxide solution of the present invention is 50 ppm to 1000 ppm, when the content is calculated for chlorine dioxide, and is preferably 100 ppm to 800 ppm. If the concentration of chlorine dioxide is lower than 50 ppm, the deodorizing and sterilizing effects are reduced. The chlorine dioxide that is used by the device of the present invention can be replaced with ozone.

When a heated air stream or an air stream at ordinary temperature that contains citric acid is passed through the ceramic body that is impregnated with a stabilized chlorine dioxide solution, the generation of chlorine dioxide gas is accelerated and the content of the chlorine dioxide gas in the air stream can be increased.

The ceramic used in the present invention is alkaline ceramic and preferably contains at least one material selected from a group consisting of animal bone powder, shell powder, limestone powder, and coral powder.

In addition, the alkaline ceramic contains at least one ceramic selected from a group consisting of silica, alumina and zeolite.

Taking the absorption capability of an alkaline solution into account, a ceramic that contains powdered animal bones is desirable; moreover, when taking absorption speed into account, a ceramic wherein the proportion of powdered animal bones is high, for example, 50 to 80 weight %, is more desirable. The powdered animal bones can be replaced with another alkaline adsorbent that has a high alkaline solution absorption capability.

An additional agent, such as a binder or a filling agent, is added to these ceramics, as necessary, to form a ceramic body for the present invention.

The powdered animal bones described above are mainly those that are acquired by processing crude bones, especially the bones of cows, horses and sheep, that are commonly disposed of on farms, etc.

The crude bones are cut into an appropriate size for a calcination process, boiled, and calcined at around 900° C. to 1100° C. Since oxidized putrefaction occurs on bones if organic substances, such as gelatin, fat, protein and glue, that are not components of bone remain, such substances must be completely eliminated.

During the boiling process, most organic substances that are attached not only to the external walls of bones but also inside pores along the surface of bones can be removed.

When the calcination process is then performed, the remaining organic substances can be removed completely, and simultaneously the humidity (water content) of the bone can be reduced to several percent or less, preferably to almost 0%.

Dependent on the calcining conditions, the bone is dried and maintains its original organization, which includes multiple fine pores. After the bone is cooled, it is crushed and then pulverized, and is formed into a bone powder having a size of about 20 to 200 mesh, more preferably 50 to 100 mesh, by a powdering machine.

The powdered bone has a yield of about 40 weight % of the original crude bone. The composition of the particles includes calcium (about 33 weight %) as a main component, phosphorus (about 16.7 weight %), barium (about 1.03 weight %), sodium (about 0.76 weight %), sulfur (about 0.64 weight %), and some magnesium, potassium, chlorine, amine, iron, and others. Multiple micropores communicate with each other both on the internal and external sides of the particles, which are alkaline.

Bentonite, Japanese acid clay, activated clay, kaolin clay, sericite, pyrophyllite, refractory clay, montmorillonite, or the like may be employed as a binder.

A ceramic body that has multiple micropores absorbs a solution well due to capillary action, and permits the solution to permeate it easily. In addition, when air contacts such a ceramic body, the generation of chlorine dioxide gas is accelerated.

In this invention, the ceramic body can be formed arbitrarily, as a particulate, or as a spherical or a columnar body, so long as the ceramic body can be impregnated with a citric acid solution or an alkaline chlorine dioxide solution. But taking into consideration the impregnation by the solution, the discharge of chlorine dioxide gas, and the convenience of the device design, a columnar ceramic body is preferable.

With the above described arrangement, air at normal temperature, or around 40° C., that contains alkaline chlorine dioxide gas, which is generated by the alkaline chlorine dioxide gas generator 13, is supplied through the hose 3 to the air mattress 2, which it fills evenly, and is then discharged through minute discharge holes in the surface of the air mattress 2 at around 23° C.

By employing the synergistic effect that is acquired by combining chlorine dioxide gas, warm air and alkaline air, the patient's body is prevented from becoming hot and damp by bathing almost all portions of it with the gas. Furthermore, an injured portion of a patient's body can be dried and sterilized, and healed, and the propagation of contagion can be prevented, so that effective sterilization is performed and care providers and nursing personnel can be protected from germ and viral infections.

Also performed is the deodorization, sterilization, and drying of the underwear and bedclothes of bedridden elderly persons, or patients with advanced diseases, so that the load placed on care providers or nursing personnel can be reduced.

The surface of an air mattress that is available on the market has a wave shape, and the surface can be caused to undulate by alternately raising and lowering surface segments using two air streams supplied by an air generator.

For the present invention, such an air mattress is employed to reduce the area of the mattress that contacts a body and to prevent the occurrence of an interruption in the circulation of the blood, so that the prevention of decubitus ulcers is more effectively performed.

Since the concentration of chlorine dioxide gas that is contained in the air that is discharged from the air mattress 2 is 1000 ppm or lower, it is harmless to human beings, and purifies the atmosphere through a deodorization process.

With the thus arranged components of the present invention, the easy supply of air for deodorization and sterilization is ensured, and with this air, a patient's body, and clothing and bedding can be dried, deodorized and sterilized so that they are kept clean, and so that the occurrence of decubitus ulcers is prevented.

According to the present invention, the propagation of contagion is prevented, effective sterilization is performed, and care providers and nursing personnel are protected from viral infections.

Experiment I

A mixture that consisted of 60 weight % of 100-mesh powdered cow bone, 20 weight % of silica, and 20 weight % of alumina, were formed into a spherical ceramic body having a diameter of about 18 mm.

The thus obtained ceramic body was heated to about 80° C. The resultant ceramic body was immersed in an alkaline chlorine dioxide solution at normal temperature for 10 to 60 seconds, and was then extracted to acquire a ceramic body that was impregnated with the alkaline chlorine dioxide solution.

In the same manner, another ceramic body was immersed at normal temperature in a citric acid solution, which had an adjusted pH value of about pH 4, for 10 to 60 seconds, and was then extracted to acquire a ceramic body that was impregnated with the citric acid solution.

Figure 13A:
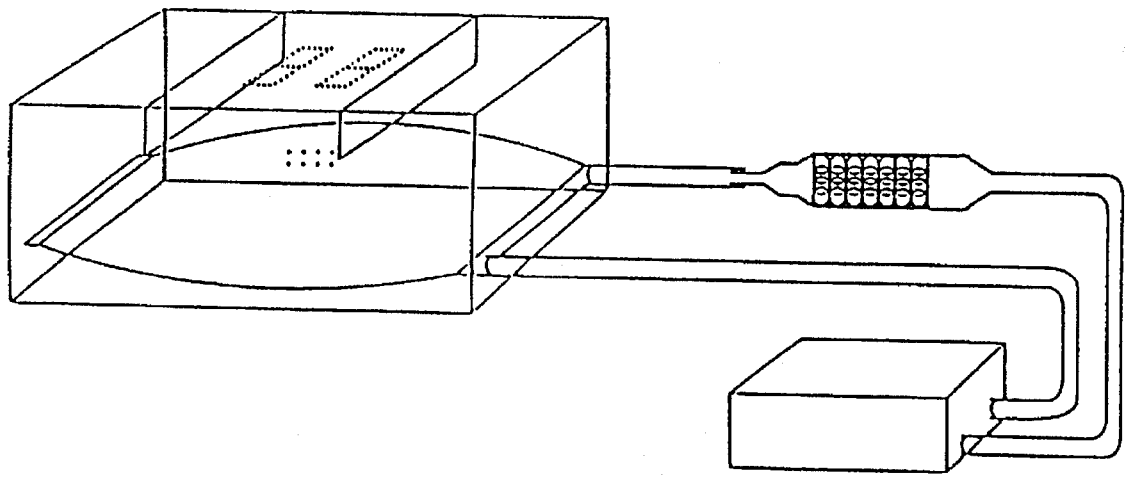
FIGS. 13A and 13B are diagrams showing device models according to the present invention that were produced for the sterilization effect experiments and for the measurement of the remaining amount of chlorine dioxide.
Figure 13B:
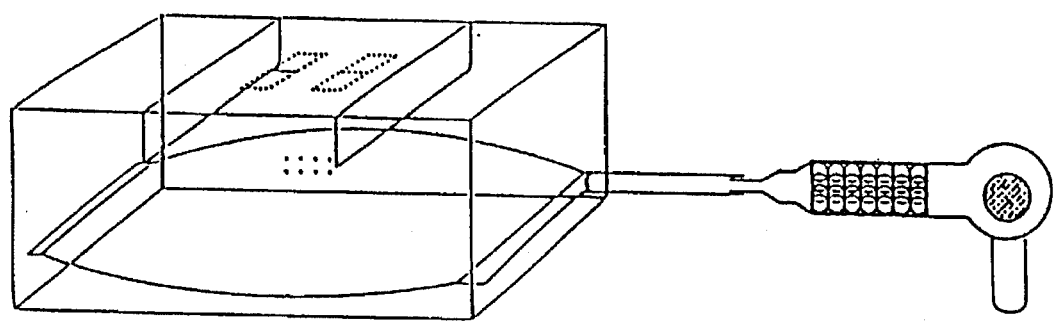
Figure 16:
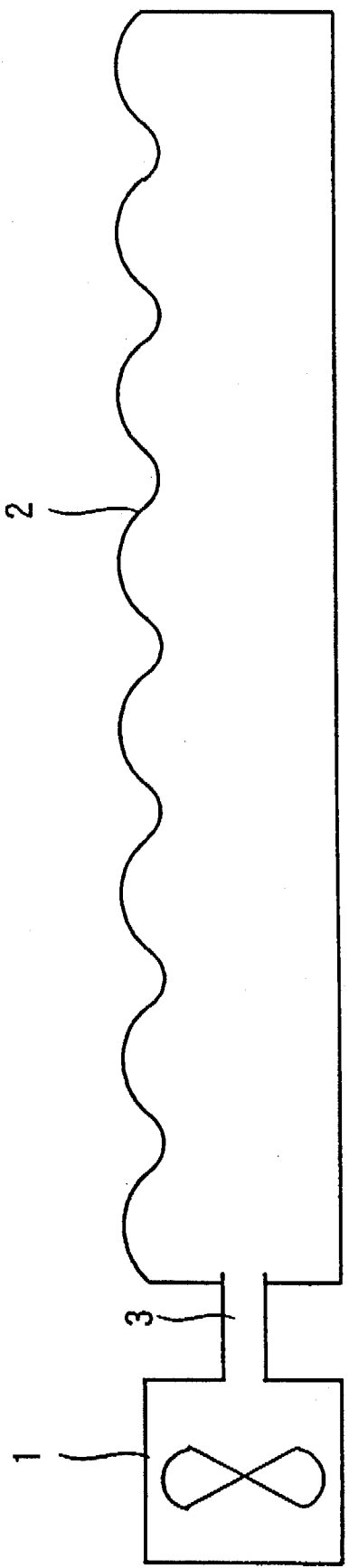
FIG. 16 is a diagram illustrating the arrangement of a conventional decubitus ulcer prevention device.

As is shown in FIGS. 13A and 13B, the thus obtained ceramic body that was impregnated with the citric acid solution was located adjacent to the fan of a dryer, while the ceramic body that was impregnated with the alkaline chlorine dioxide solution was located adjacent to the outlet of the dryer. The outlet of the dryer was connected to a vinyl bag and a plurality of small holes were formed in the top of the bag, so that the gas from the dryer could be discharged.

It should be noted that the device shown in FIG. 13A had a hose for absorbing the gas in the bag, so as to adjust the amount of gas that was transmitted to the bag.

The present applicant delegated to Nihon Shokuhin Analysis Center Foundation the performance of the experiments to determine the sterilization effects obtained by the use of the two thus structured dryer models (A and B).

At the Center, a culture fluid was employed to acquire test germs. The germs were grown in a shake culture, which was held at 35° C. for 16 to 24 hours, for which was used a bouillon culture medium (NB culture medium) to which was added a 0.2% meat extract of Pseudomonas seruginosa IFO 13275 and Staphylococcus aurers IFO 12732. Using a sterilized phosphoric buffer solution, the culture fluid was diluted to one tenth of its original strength, with the resultant fluid serving as a germ fluid. Gauze pads were then permeated with 0.2 ml of the germ fluid.

As is shown in FIGS. 13A and 13B, four such gauze pads were fastened to the ceiling of an acrylic case and the dryer was driven. The gauze pads were collected at intervals of 20 minutes, one hour, two hours, three hours, and four hours following the activation of the dryer, and were washed well with 10 ml of a soybean casein digest (SCDLP) culture medium. The number of activated germs in the fluid was measured by the pour-plate culture method (a 48-hour culture held at 35° C.) that employed the SCDLP culture medium.

For comparison purposes, the ceramic body that was impregnated with distilled water was employed.

As a result, as is shown in FIG. 14, while for the dryer model of the present invention Pseudomonas seruginosa IFO 13275 was not detected at an interval of two hours following the activation, a considerable number of germs was detected for the comparison dryer model even after an interval of four hours.

Similarly, while for the dryer model of the present invention activated germs were not detected two hours following the activation of the dryer, activated germs were detected for the comparison dryer model after three hours had elapsed.

Experiment 2

Also at the Center, the measurement of the remaining amount of chlorine dioxide was conducted by using the models shown in FIGS. 13A and 13B for the device of the present invention.

In the same manner as in experiment 1, the ceramic body that was impregnated with a citric acid solution and the ceramic body that was impregnated with an alkaline chlorine dioxide solution were provided. Alkaline chlorine dioxide gas from the dryer was blown through the small holes in the top of the bag against gauze pads that were attached to the ceiling of an acrylic case. Then, the gauze pads were collected at intervals of 20 minutes, one hour, two hours, and three hours following the activation of the dryer, and were immersed in 10 ml of refined water. Droplets of an Ortho-tolidin solution were added to the immersing fluid, and five minutes later color reaction was detected with the naked eye.

As a result, as is shown in FIG. 15, chlorine dioxide was not detected for the intervals of 20 minutes, one hour, two hours, and three hours following the activation of the dryer model.

Various modes of carrying out the invention are contemplated as being within the scope of the following claims that particularly point out and distinctly claim the subject matter regarded as the invention.

What is claimed is:

1. A decubitus ulcer prevention device comprising:
    an air generator having a fan,
    an air mattress for receiving air, from said air generator, that is discharged at a surface through minute air discharge holes, and
    a hose for connecting said air mattress to said air generator,
    wherein, along a flow path of said air that passes through said fan, are located, in order as named, a heater and an alkaline chlorine dioxide gas generator, in which is internally provided a ceramic body that is impregnated with an alkaline chlorine dioxide solution, whereby air that is heated, by passing through said heater, is brought into contact with said ceramic body, so that air that includes alkaline chlorine dioxide gas is thus supplied to said air mattress.

2. A decubitus ulcer prevention device, which comprises:
    an air generator having a fan,
    an air mattress for receiving air, from said air generator, that is discharged at a surface through minute discharge holes, and
    a hose for connecting said air mattress with said air generator,
    wherein, along a flow path of said air that passes through said fan, is located an alkaline chlorine dioxide gas generator, in which a ceramic body that is impregnated with a citric acid solution is provided on a side adjacent to said fan and a ceramic body that is impregnated with an alkaline chlorine dioxide solution is provided following said ceramic body that is impregnated with a citric acid solution, whereby air that passes through said fan contacts said ceramic bodies, so that air that includes alkaline chlorine dioxide gas is thus supplied to said air mattress.

3. A decubitus ulcer prevention device according to claim 1, wherein said alkaline chlorine dioxide gas generator is stored detachably in said air generator.

4. A decubitus ulcer prevention device according to claim 1, wherein said alkaline chlorine dioxide gas generator is installed outside said air generator and is so connected to said hose as to be detachable.

5. A decubitus ulcer prevention device according to claim 1, wherein a unit for supplying an alkaline chlorine dioxide solution to said ceramic body is detachably attached to said alkaline chlorine dioxide gas generator, and formed in said ceramic body is a solution supply groove for supplying said alkaline chlorine dioxide solution to a surrounding side portion of said ceramic body.

6. A decubitus ulcer prevention device according to claim 2, wherein a unit for supplying a citric acid solution to said ceramic body is detachably attached to said alkaline chlorine dioxide gas generator, and formed in said ceramic body is a solution supply groove for supplying said citric acid solution to a surrounding side portion of said ceramic body.

7. A decubitus ulcer prevention device according to claim 1, wherein said alkaline chlorine dioxide solution that is used to permeate said ceramic body, which is impregnated with said alkaline chlorine dioxide solution, has a calculated chlorine dioxide content of 50 ppm to 1000 ppm.

8. A decubitus ulcer prevention device according to claim 2, wherein said citric acid solution that is used to permeate said ceramic body is adjusted to pH 2 to pH 5.

9. A decubitus ulcer prevention device according to claim 1, wherein said ceramic bodies are columnar in shape, and in cross section have a plurality of longitudinal through holes.

10. A decubitus ulcer prevention device according to claim 1, wherein said ceramic bodies are formed from alkaline ceramics that contain at least one material selected from a group consisting of animal bone powder, shell powder, limestone powder, and coral powder.

11. A decubitus ulcer prevention device according to claim 10, wherein said alkaline ceramic contains animal bone powder as the main activated element.

12. A decubitus ulcer prevention device according to claim 10, wherein said alkaline ceramic contains at least one ceramic selected from a group consisting of silica gel, alumina, and zeolite.

13. A decubitus ulcer prevention device according to claim 2, wherein said alkaline chlorine dioxide gas generator is stored detachably in said air generator.

14. A decubitus ulcer prevention device according to claim 2, wherein said alkaline chlorine dioxide gas generator is installed outside said air generator and is so connected to said hose as to be detachable.

15. A decubitus ulcer prevention device according to claim 2, wherein a unit for supplying an alkaline chlorine dioxide solution to said ceramic body is detachably attached to said alkaline chlorine dioxide gas generator, and formed in said ceramic body is a solution supply groove for supplying said alkaline chlorine dioxide solution to a surrounding side portion of said ceramic body.

16. A decubitus ulcer prevention device according to claim 2, wherein said alkaline chlorine dioxide solution that is used to permeate said ceramic body, which is impregnated with said alkaline chlorine dioxide solution, has a calculated chlorine dioxide content of 50 ppm to 1000 ppm.

17. A decubitus ulcer prevention device according to claim 2, wherein said ceramic bodies are columnar in shape, and in cross section have a plurality of longitudinal through holes.

18. A decubitus ulcer prevention device according to claim 2, wherein said ceramic bodies are formed from alkaline ceramics that contain at least one material selected from a group consisting of animal bone powder, shell powder, limestone powder, and coral powder.

19. A decubitus ulcer prevention device according to claim 18, wherein said alkaline ceramic contains animal bone powder as the main activated element.

20. A decubitus ulcer prevention device according to claim 18, wherein said alkaline ceramic contains at least one ceramic selected from a group consisting of silica gel, alumina, and zeolite.

* * * * *